(12) United States Patent
Campbell et al.

(10) Patent No.: US 7,332,460 B2
(45) Date of Patent: *Feb. 19, 2008

(54) ALKYLXYLENE SULFONATES FOR ENHANCED OIL RECOVERY PROCESSES

(75) Inventors: Curt B. Campbell, Hercules, CA (US); Gilles P. Sinquin, Richmond, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/893,729

(22) Filed: Jul. 15, 2004

(65) Prior Publication Data

US 2006/0014650 A1    Jan. 19, 2006

(51) Int. Cl.
  C09K 8/584 (2006.01)
  C07C 313/00 (2006.01)
  E21B 21/14 (2006.01)

(52) U.S. Cl. ............ 507/259; 507/203; 507/252; 507/256; 562/45; 562/91

(58) Field of Classification Search ............ 507/259; 562/91
  See application file for complete search history.

(56) References Cited

U.S. PATENT DOCUMENTS

| | | | |
|---|---|---|---|
| 2,467,131 A * | 4/1949 | Madison et al. | 562/91 |
| 2,467,132 A * | 4/1949 | Madison et al. | 562/91 |
| 2,796,429 A * | 6/1957 | Kooijman et al. | 562/84 |
| 3,601,198 A | 8/1971 | Aheam et al. | |
| 4,005,749 A | 2/1977 | Birk et al. | |
| 4,067,818 A * | 1/1978 | Marin | 252/88.1 |
| 4,217,958 A | 8/1980 | Doster et al. | |
| 4,452,308 A | 6/1984 | Haskin et al. | |
| 4,452,708 A | 6/1984 | Aldrich et al. | |
| 4,476,929 A | 10/1984 | Stapp | |
| 4,589,489 A | 5/1986 | Volz et al. | |
| 4,608,204 A | 8/1986 | Lew et al. | |
| 4,690,785 A | 9/1987 | Mausner et al. | |
| 4,873,025 A | 10/1989 | Bolsman | |
| 4,932,473 A | 6/1990 | Borchardt | |
| 6,022,834 A | 2/2000 | Hsu et al. | |
| 6,043,391 A | 3/2000 | Berger et al. | |
| 6,269,881 B1 | 8/2001 | Chou et al. | |

FOREIGN PATENT DOCUMENTS

| | | |
|---|---|---|
| EP | 0 111 354 B1 | 12/1986 |
| EP | 0 148 517 B1 | 9/1988 |
| EP | 0 158 486 B1 | 12/1988 |
| EP | 0 413 374 B1 | 4/1994 |
| GB | 2 138 866 A | 10/1984 |
| WO | WO 01/98432 A2 | 12/2001 |

* cited by examiner

*Primary Examiner*—Randy Gulakowski
*Assistant Examiner*—Timothy J. Kugel
(74) *Attorney, Agent, or Firm*—Sarita R. Kelley

(57) ABSTRACT

The present invention is directed to alkylxylene sulfonate for enhanced oil recovery processes. The alkylxylene moiety in the alkylxylene sulfonate contains a high percentage of the 4-alkyl-1,2-dimethyl benzene isomer and a high percentage of alkyl group attachment to the xylene ring at positions higher than the 2-position on the alkyl carbon chain. The present invention is also directed to a method for enhancing the recovery of oil from a subterranean reservoir which method employs the alkylxylene sulfonate of the present invention. The alkylxylene sulfonate is employed in an aqueous media. The method optionally employs co-surfactants. It has surprisingly been discovered that the high percentage of the 4-alkyl-1,2-dimethyl benzene isomer and the high percentage alkyl group attachment to the xylene moiety at positions higher than the 2-position along the alkyl carbon chain on the alkylxylene sulfonate of the present invention provides an enhanced oil recovery (EOR) surfactant having low Interfacial Tension (IFT).

16 Claims, 3 Drawing Sheets

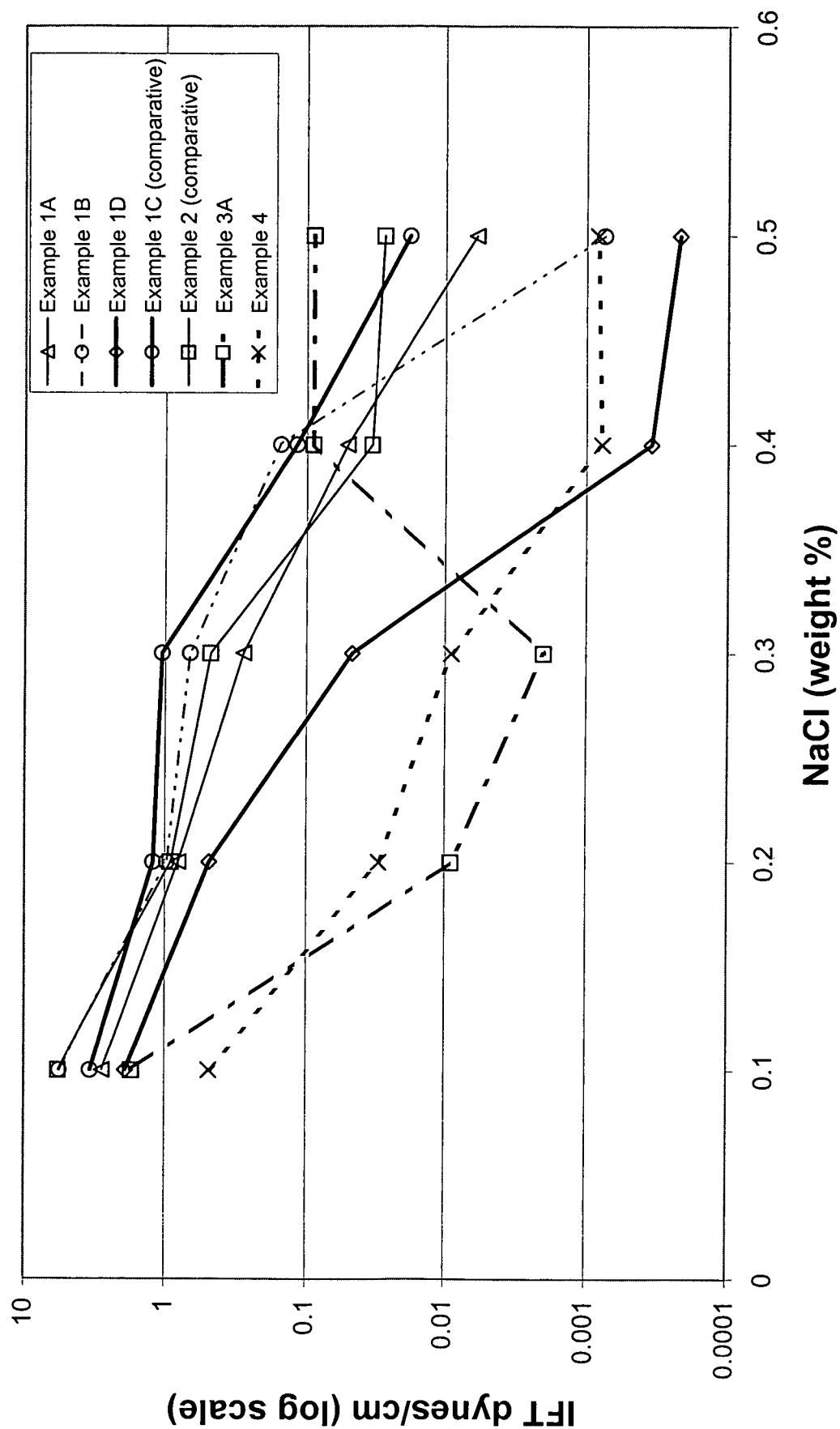

ALKYLXYLENE SULFONATES FOR ENHANCED OIL RECOVERY PROCESSES

The present invention is directed to alkylxylene sulfonate for enhanced oil recovery processes. The alkylxylene moiety in the alkylxylene sulfonate contains a high percentage of the 4-alkyl-1,2-dimethyl benzene isomer and attachment of the alkyl group to the xylene ring at positions higher than the 2-position on the alkyl carbon chain. The present invention is also directed to a method for enhancing the recovery of oil from a subterranean reservoir which method employs the alkylxylene sulfonate of the present invention. The alkylxylene sulfonate is employed in an aqueous media. The method optionally employs co-surfactants.

BACKGROUND OF THE INVENTION

Crude oil production from oil in subterranean reservoirs may involve use of various flooding methods as the natural forces that are used in the "primary recovery" process become depleted. A large portion of the crude oil may have to be driven out of the formation in "secondary" or "tertiary" recovery processes. In addition, some reservoirs may not have sufficient natural forces for oil production even by primary recovery processes. The production of crude oil using such flooding methods is one example of enhanced oil recovery process.

One trend in the petroleum industry now is to plan exploitation of the oil field at the beginning of the project. Injecting a displacing fluid or gas may begin early, long before the complete depletion of the field by primary recovery processes. Methods for improving displacement efficiency or sweep efficiency may be used at the very beginning of the first injection of a displacing fluid or gas, rather than under secondary and tertiary recovery conditions.

The least expensive and easiest method of flooding a subterranean reservoir 2 for the production of crude oil is by injecting a liquid or a gas into the well to force the oil to the surface. Water flooding is the most widely used fluid. However, water does not readily displace oil because of the immiscibility of water and oil and/or the high interfacial tension between the two liquids.

The addition of chemicals to modify the properties of the flooding liquid is well known in the art. Surfactants are one class of chemical compounds that have been used in aqueous media for enhanced oil recovery. Surfactants have been found to effectively lower the interfacial tension between oil and water and enabling the oil droplets to flow more easily through the channels of the reservoir.

Alkylaryl sulfonates have been used as surfactants for enhanced oil recovery. They have been used in surfactant flooding, alone, or in conjunction with co-surfactants and/or sacrificial agents. Alkylaryl sulfonates are generally used not only because they are able to lower the interfacial tension between oil and water, but also because when used in conjunction with varying amounts of sodium chloride they exhibit different phase behavior. At low salinity, alkylaryl sulfonates can have a tendency to stay in the aqueous phase, but at high salinity they tend to stay in the oil phase. Around mid-point salinity, a micro-emulsion forms in which appreciable amounts of oil and brine are in the micro-emulsion phase. It is at this mid-point salinity that the surfactant exhibits high oil recovery potential. The salinity of the water in subterranean hydrocarbon reservoirs may vary a great deal, for example, the Minas oil field in Indonesia has total dissolved salts of between 0.2 and 0.3 weight percent. Other reservoirs may have salinities as high as or higher than 2.0 percent sodium chloride and over 0.5 percent calcium chloride and magnesium chloride. It is desirable to optimize the alkylaryl sulfonates for surfactant flooding for enhanced oil recovery for a particular reservoir by determining the interfacial tension of the reservoir oil in an aqueous brine solution containing the alkylaryl sulfonates which matches the salinity of the reservoir water.

Generally, pure alkylaryl sulfonates, that is, those having a narrow range of molecular weights, are useful for recovery of light crude oils. Such alkylaryl sulfonates have been less useful for enhancing oil recovery of crude oils containing high wax content. Alkylaryl sulfonates having a broad spectrum of carbon chain lengths in the alkyl group are more desirable for use to recover waxy crude oils.

A number of patents and patent applications have discussed methods for enhanced oil recovery using surfactant flooding. In addition to the use of surfactants, there are a number of patent and patent applications discussing the use of co-surfactants and sacrificial agents for enhanced oil recovery.

EP 0 111 354 B1 discloses the use of alkylxylene sulfonate compounds derived from alkyl meta- and para-xylenes in methods for displacing oil from reservoirs of relatively higher salinities than those to which the conventional alkyl ortho-xylene sulfonate compounds are limited.

EP 0 148 517 B1 discloses olefin sulfonate compositions comprising an aqueous solution containing 15 to 35 weight percent of a blend of $C_{12}$-$C_{22}$ linear alpha-olefin and an alkylaryl sulfonate wherein the aryl group is benzene, toluene or xylene. The compositions are used in foam drive processes for enhanced oil recovery.

EP 0 158 486 B1 discloses the use of polyalkyl aromatic sulfonates, particularly dialkyl aromatic sulfonates in steam recovery methods for enhancing oil recovery. The increase of the ratio of para-isomer to meta-isomer results in a significantly more hydrolytically, thermally stable surfactant under steam recovery operating conditions.

EP 0 413 374 B1 discloses the use of alkylxylene sulfonates and a glycol for enhanced oil recovery. The alkyl group containing 8 to 30 carbon atoms is attached to the aromatic ring from its 2-position to its mid-position. The glycol is used as a sacrificial agent.

GB 2 138 866 A discloses a micellar slug for use in the recovery of oil consisting essentially of a hydrocarbon, an aqueous medium, a surfactant and a co-surfactant. The surfactant containing, as essential constituents, an internal olefin sulfonate having 10 to 26 carbon atoms and at least one ethoxylate. The micellar slug has an improved salinity tolerance and hard-water resistance and is capable of forming micro-emulsions having low interfacial tension and good stability.

U.S. Pat. No. 3,601,198 discloses the use of oil-soluble anionic surface-active agents or detergents, such as sulfonates, petroleum and synthetic, for a hydraulic fracturing operation. The synthetic sulfonates are alkaline earth metal salts of high molecular weight sulfonic acids and are produced using aromatics, such as benzene, toluene, xylene and naphthalene. The molecular weights of the sulfonates are in the range between 300 and about 750.

U.S. Pat. No. 4,005,749 discloses the use of polyalkylene oxides as sacrificial agents prior to surfactant flooding in enhanced oil recovery process. The polyalkylene oxides have molecular weights of at least 1,200. The surfactant flood is an aqueous slug containing a surfactant exhibiting a lower molecular weight than that of the polyalkylene oxides.

The sacrificial agent may also be used along with the surfactant flooding, but its concentration is lower than when used as a sacrificial agent.

U.S. Pat. No. 4,217,958 discloses the use of sacrificial agents, polybasic carboxylic acid or their water soluble salts, in admixture with a chemical oil recovery agent, such as a surfactant, a polymer, and/or a micellar dispersion to reduce the adsorption of surfactants and/or the polymers on reservoir rock.

U.S. Pat. No. 4,452,708 discloses an oil recovery method using a particular class of alkylaryl sulfonate surfactants. The surfactants are derived from an extracted aromatic feedstock consisting essentially of benzene, toluene, xylene and lesser amounts of alkylbenzene alkylated with linear alpha-olefins to favor second-carbon attachment. The sulfonates have high oil solubilization parameters and their phase behavior is substantially independent of temperature over 120° F.-250° F.

U.S. Pat. No. 4,476,929 discloses the use of co-surfactants, a sulfoxide, having a maximum of 14 carbon atoms, in surfactant systems for enhanced oil recovery processes. The preferred surfactant is a petroleum sulfonate having average equivalent weights in the range of about 325 to 500.

U.S. Pat. No. 4,452,308 discloses the use of polyalkylene glycols or copolymers thereof having molecular weights between 100 and 1,200 with chemical flooding. The concentration of the polyalkylene glycols used is 0.01-0.5 weight percent. The preferred polyalkylene glycols are polyethylene and polypropylene glycols.

U.S. Pat. No. 4,589,489 discloses the use of polyalkylene glycols or their copolymers for surfactant flooding or for preflushing. It is preferred to use polyethylene glycol having a molecular weight of from 800 to about 1,100. The concentration used is dependent on the subterranean formation, for example, between 1-100 kilograms per cubic meter.

U.S. Pat. No. 4,608,204 discloses a process for the preparation of a low viscosity aqueous alkyltoluene or alkylxylene sulfonate with the addition of sodium chloride during neutralization or after neutralization. Such low viscosity sulfonates are useful as surfactants in enhanced oil recovery processes. When xylene is employed, a mixture of the three isomers, ortho-, meta- and para-, are preferred.

U.S. Pat. No. 4,690,785 discloses low water neutralization energy-saving process to produce highly active alkylaryl sulfonate by combining an alkylaryl sulfonic acid with a salt-forming base, and utilizing the heat generated during the neutralization reaction to drive off the water present in the reaction mixture. The resulting free flowing alkylaryl sulfonate powder is at least 90 percent active. When dissolved in water, the powdered product will have a pH of about 4.6 to about 11.5, usually about 7 or about 8.

U.S. Pat. No. 4,873,025 discloses compositions comprising alkylxylene sulfonates in which a substantial portion of the alkylxylene sulfonate fraction has $C_6$-$C_{20}$ substituents, positioned directly opposite to the sulfonate moiety. Such compositions are derived from para-xylene or isomer mixtures comprising substantially para-xylene. These alkylxylene sulfonates are useful as surfactants, particularly in enhanced oil recovery techniques.

U.S. Pat. No. 4,932,473 discloses a process for enhanced oil recovery employing one or more alkyltoluene sulfonates in a saline aqueous solution. The improvement comprises including into the said solutions one or more alkylpolysaccharide surfactants for enhancing the solubility of the alkyltoluene sulfonate. The composition enhances calcium and sodium ion tolerance of the alkyltoluene sulfonates.

U.S. Pat. No. 6,022,834 discloses an improved alkali surfactant flood process with ultra-low interfacial tension. The surfactant system contains (1) a mixture of anionic surfactants; (2) solvent(s); (3) a strong base; and (4) optionally, a nonionic surfactant or mixtures of nonionic surfactants or sulfates or carboxylates of these nonionic surfactants. The anionic surfactants are sulfonates derived from alkylbenzene, alkylnaphthalene, alkyltoluene or alkylxylene. The alkyl group consists of between about $C_4$ and about $C_{24}$.

U.S. Pat. No. 6,043,391 discloses new anionic surfactants and their method of preparation by simultaneously sulfonating and alkylating an aromatic hydrocarbon. The one-step preparation process involves sulfonating an alpha-olefin with $SO_3$, followed by repeated hydrolysis and dehydration with water which results in the formation of an alkene sulfonic acid. This strong acid is then used to alkylate aromatic compounds. Additional strong acid catalyst is beneficial to obtain useful yields of the final product.

U.S. Pat. No. 6,269,881 discloses an oil recovery process using a particular class of alkylaryl sulfonates derived from an alpha-olefin stream having a broad distribution of even carbon numbers ranging from 12 to 58. The aromatic hydrocarbons used to produce the alkylaryl sulfonates may be benzene, toluene, xylene or mixtures thereof. The surfactant has ultra low interfacial tension with waxy crude oils.

WO 01/98432 A2 discloses a surfactant blend for lowering the interfacial tension between oil and aqueous fluid for enhanced oil recovery. The blend comprises at least one synthetic polyisobutylene and at least one surfactant consisting of sulfonate surfactants, alcohols and non-ionic surfactants.

A general treatise on enhanced oil recovery is *Basic Concepts in Enhanced Oil Recovery Processes* edited by M. Baviere (published for SCI by Elsevier Applied Science, London and New York, 1991).

SUMMARY OF THE INVENTION

The present invention is directed to alkylxylene sulfonate for enhanced oil recovery (EOR) processes. The alkylxylene moiety in the alkylxylene sulfonate of the present invention contains greater than 70 percent of the 4-alkyl-1,2-dimethyl benzene isomer and wherein the attachment on the alkyl carbon chain to the xylene moiety at positions higher than the 2-position on the alkyl carbon chain is at least 40 percent. The present invention is also directed to a method for enhancing the recovery of oil from a subterranean reservoir which method employs the alkylxylene sulfonate of the present invention. The alkylxylene sulfonate is employed in an aqueous media. The method optionally employs co-surfactants, such as alcohols, alcohol ethers, polyalkylene glycols, poly(oxyalkylene)glycols and poly(oxyalkylene)glycol ethers, or mixtures thereof.

It has been discovered that the alkylxylene moiety in the alkylxylene sulfonate of the present invention containing greater than 70 percent of the 4-alkyl-1,2-dimethyl benzene isomer and wherein the attachment of the alkyl group to the xylene moiety in the alkylxylene sulfonate at positions higher than the 2-position along the alkyl carbon chain is at least 40 percent provide an EOR surfactant having low Interfacial Tension (IFT).

In particular, the present invention is directed to alkylxylene sulfonate for enhanced oil recovery processes having the general formula:

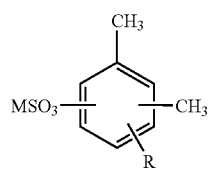

wherein R is an alkyl group containing from about 10 to about 58 carbon atoms, M is a mono-valent cation, and the alkylxylene moiety in the alkylxylene sulfonate is alkyl-ortho-xylene in at least 85 percent of the total alkylxylene sulfonate, and wherein the alkylxylene moiety in the alkylxylene sulfonate contains greater than about 70 percent of the 4-alkyl-1,2-dimethyl benzene isomer and the attachment of the alkyl group to the xylene moiety in the alkylxylene sulfonate is at positions higher than the 2-position along the alkyl chain in at least 40 percent of the total alkylxylene sulfonate of the present invention.

Preferably, the alkylxylene moiety is alkyl-ortho-xylene in at least 95 percent of the total alkylxylene sulfonate.

Preferably, the alkylxylene moiety in the alkylxylene sulfonate contains greater than about 80 percent of the 4-alkyl-1,2-dimethyl benzene isomer. More preferably, the alkylxylene moiety in the alkylxylene sulfonate contains at least 90 percent of the 4-alkyl-1,2-dimethyl benzene isomer. The structures for the 4-alkyl-1,2-dimethyl benzene and the 3-alkyl-1,2-dimethyl benzene are given below.

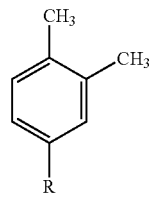
4-alkyl-1,2dimethylbenzene

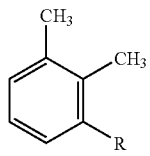
3-alkyl-1,2-dimethylbenzene

Preferably, the attachment of the alkyl group to the xylene moiety is at positions higher than the 2-position along the alkyl chain in at least 45 percent of the total alkylxylene sulfonate and more preferably the attachment of the alkyl group to the xylene moiety is at positions higher than the 2-position along the alkyl chain in at least 60 percent of the total alkylxylene sulfonate. The structures for the various attachment positions on the carbon chain of the alkyl group to the xylene moiety are given below.

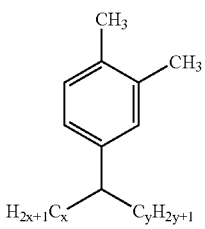
4-alkyl-1,2-dimethylbenzene

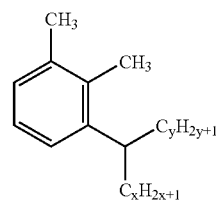
3-alkyl-1,2-dimethylbenzene

In the above structures, the values of x and y determine the attachment position of the alkyl group to the xylene moiety on the carbon chain. For example, for a $C_{1-2}$ alkyl group, the value of x equal to 2 and y equal to 9 corresponds to the attachment of the alkyl group at the 3-position on the alkyl carbon chain. Thus, for x+y+1 equal to between 10 and 58, knowing x and y provides the attachment of the alkyl group to the xylene moiety for the corresponding chain lengths between $C_{10}$ and $C_{58}$.

The mono-valent cation in the alkylxylene sulfonate is an alkali metal. Preferably, the alkali metal is sodium. The mono-valent cation may be an ammonium ion or an organic ammonium ion.

The alkyl group in the alkylxylene sulfonate of the present invention is derived from a linear alpha olefin or isomerized olefin containing from about 10 to about 58 carbon atoms. Preferably, the alkyl group is derived from a linear alpha olefin or isomerized olefin containing from about 10 to about 40 carbon atoms. More preferably, the alkyl group is derived from a linear alpha olefin or isomerized olefin containing from about 12 to about 30 carbon atoms.

The alkyl group in the above alkylxylene sulfonate contains a broad distribution of alkyl chain lengths. The upper heavier range $C_{32}$ to $C_{58}$ may comprise from about 5 percent to about 15 percent of the alkyl groups and more preferably from about 8 percent to about 12 percent of the alkyl groups. A preferred distribution of alkyl chain lengths comprises from about 40 to about 80 percent $C_{12}$ to $C_{20}$. A more preferred distribution of alkyl chain lengths comprises from about 50 to about 70 percent $C_{12}$ to $C_{20}$.

Another embodiment of the present invention is directed to alkylxylene sulfonate for enhanced oil recovery processes, which composition is derived from ortho-, meta- and para-xylene, and wherein the alkyl group contains from about 10 to about 58 carbon atoms, and the alkylxylene moiety in the alkylxylene sulfonate is alkyl-ortho-xylene in at least 85 percent of the total alkylxylene sulfonate, and wherein the alkylxylene moiety in the alkylxylene sulfonate contains greater than about 70 percent of the 4-alkyl-1,2-dimethyl benzene isomer and the attachment of the alkyl group to the xylene moiety in the alkylxylene sulfonate is at positions higher than the 2-position along the alkyl chain in at least 40 percent of the total alkylxylene sulfonate of the present invention.

Preferably, the alkylxylene moiety in the alkylxylene sulfonate is alkyl-ortho-xylene in at least 95 percent of the total alkylxylene sulfonate.

Preferably, the alkylxylene moiety in the alkylxylene sulfonate contains greater than about 80 percent of the 4-alkyl-1,2-dimethyl benzene isomer. More preferably, the alkylxylene moiety in the alkylxylene sulfonate contains at least 90 percent of the 4-alkyl-1,2-dimethyl benzene isomer. The structures for the 4-alkyl-1,2-dimethyl benzene and the 3-alkyl-1,2-dimethyl benzene are given below.

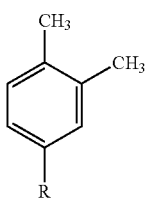
4-alkyl-1,2dimethylbenzene

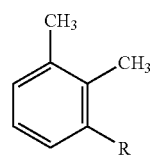
3-alkyl-1,2-dimethylbenzene

Preferably, the attachment of the alkyl group to the xylene moiety in the above alkylxylene sulfonate is at positions higher than the 2-position along the alkyl chain in at least 45 percent of the total alkylxylene sulfonate. More preferably, the attachment of the alkyl group to the xylene moiety is at positions higher than the 2-position along the alkyl chain in at least 60 percent of the total alkylxylene sulfonate. The structures for the various attachment positions on the carbon chain of the alkyl group to the xylene moiety are given below.

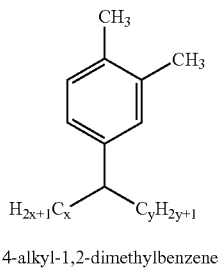

4-alkyl-1,2-dimethylbenzene

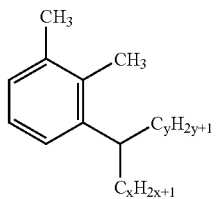

3-alkyl-1,2-dimethylbenzene

In the above structures, the values of x and y determine the attachment position of the alkyl group to the xylene moiety on the carbon chain. For example, for a $C_{12}$ alkyl group, the value of x equal to 2 and y equal to 9 corresponds to the attachment of the alkyl group at the 3-position on the alkyl carbon chain. Thus, for x+y+1 equal to between 10 and 58, knowing x and y provides the attachment of the alkyl group to the xylene moiety for the corresponding chain lengths between $C_{10}$ and $C_{58}$.

The mono-valent cation in the alkylxylene sulfonate is an alkali metal. Preferably, the alkali metal is sodium. The mono-valent cation may be an ammonium ion or an organic ammonium ion.

The alkyl group in the above alkylxylene sulfonate is derived from a linear alpha olefin or an isomerized olefin containing from about 10 to about 58 carbon atoms. Preferably, the alkyl group is derived from a linear alpha olefin or an isomerized olefin containing from about 10 to about 40 carbon atoms. More preferably, the alkyl group is derived from a linear alpha olefin or an isomerized olefin containing from about 12 to about 30 carbon atoms.

The alkyl group in the above alkylxylene sulfonate contains a broad distribution of alkyl chain lengths. The upper heavier range $C_{32}$ to $C_{58}$ may comprise from about 5 percent to about 15 percent of the alkyl groups and more preferably from about 8 percent to about 12 percent of the alkyl groups. A preferred distribution of alkyl chain lengths comprises from about 40 to about 80 percent $C_{12}$ to $C_{20}$. A more preferred distribution of alkyl chain lengths comprises from about 50 to about 70 percent $C_{12}$ to $C_{20}$.

A further embodiment of the present invention is directed to a method for recovering crude oil from a subterranean hydrocarbon containing formation, which method comprises:

(a) injecting into the formation an aqueous solution containing an amount of an alkylxylene sulfonate or mixtures of alkylxylene sulfonates effective for the recovery of crude oil wherein the alkylxylene sulfonate has the general formula:

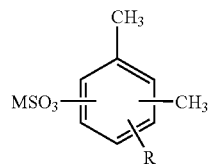

wherein R is an alkyl group containing from about 10 to about 58 carbon atoms, M is a mono-valent cation, and the alkylxylene moiety in the alkylxylene sulfonate is alkyl-ortho-xylene in at least 85 percent of the total alkylxylene sulfonate, and wherein the alkylxylene moiety in the alkylxylene sulfonate contains greater than about 70 percent of the 4-alkyl-1,2-dimethyl benzene isomer and the attachment of the alkyl group to the xylene moiety in the alkylxylene sulfonate is at positions higher than the 2-position along the alkyl chain in at least 40 percent of the total alkylxylene sulfonate of the present invention; and (b) displacing the crude oil with the aqueous solution injected into the formation to thereby recover hydrocarbons from a production well.

In step (a) in the above method, the alkylxylene sulfonate is present in the range of about 0.03 weight percent to about 2.0 weight percent of the total weight of the aqueous solution. Preferably, the composition is present in the range of about 0.1 weight percent to about 1.5 weight percent of the total weight of the aqueous composition. More preferably, the composition is present in the range of about 0.3 weight percent to about 1.0 weight percent of the total weight of the aqueous composition, and most preferably the composition is present in the range of about 0.5 weight percent to about 0.8 weight percent of the total weight of the aqueous composition.

In the above method, the alkylxylene moiety in step (a) is preferably alkyl-ortho-xylene in at least 95 percent based on the total alkylxylene sulfonate.

Preferably, the alkylxylene moiety in the alkylxylene sulfonate contains greater than about 80 percent of the 4-alkyl-1,2-dimethyl benzene isomer. More preferably, the alkylxylene moiety in the alkylxylene sulfonate contains at least 90 percent of the 4-alkyl-1,2-dimethyl benzene isomer. The structures for the 4-alkyl-1,2-dimethyl benzene and the 3-alkyl-1,2-dimethyl benzene are given below.

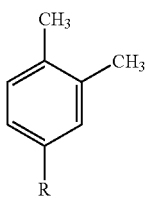

4-alkyl-1,2dimethylbenzene

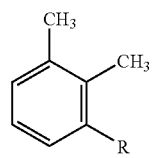

3-alkyl-1,2-dimethylbenzene

Preferably, the attachment of the alkyl group to the xylene moiety in the above alkylxylene sulfonate is at positions higher than the 2-position along the alkyl chain in at least 45 percent of the total alkylxylene sulfonate. More preferably, the attachment of the alkyl group to the xylene moiety is at positions higher than the 2-position along the alkyl chain in at least 60 percent of the total alkylxylene sulfonate. The structures for the various attachment positions on the carbon chain of the alkyl group to the xylene moiety are given below.

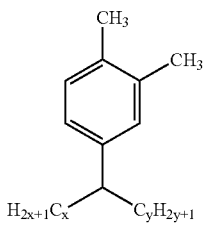

4-alkyl-1,2-dimethylbenzene

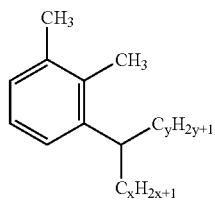

3-alkyl-1,2-dimethylbenzene

In the above structures, the values of x and y determine the attachment position of the alkyl group to the xylene moiety on the carbon chain. For example, for a $C_{12}$ alkyl group, the value of x equal to 2 and y equal to 9 corresponds to the attachment of the alkyl group at the 3-position on the alkyl carbon chain. Thus, for x+y+1 equal to between 10 and 58, knowing x and y the attachment of the alkyl group to the xylene moiety for the corresponding chain lengths between $C_{10}$ and $C_{58}$.

The mono-valent cation in step (a) in the above method is an alkali metal. Preferably, the alkali metal is sodium. The mono-valent cation may be an ammonium ion or an organic ammonium ion.

The alkyl group in step (a) of the above method is derived from a linear alpha olefin or an isomerized olefin containing from about 10 to about 58 carbon atoms. Preferably, the alkyl group is derived from a linear alpha olefin or an isomerized olefin containing from about 10 to about 40 carbon atoms. More preferably, the alkyl group is derived from a linear alpha olefin or an isomerized olefin containing from about 12 to about 30 carbon atoms.

The alkyl group in step (a) in the above method contains a broad distribution of alkyl chain lengths. The upper heavier range $C_{32}$ to $C_{58}$ may comprise from about 5 percent to about 15 percent of the alkyl groups and more preferably from about 8 percent to about 12 percent of the alkyl groups. A preferred distribution of alkyl chain lengths comprises from about 40 to about 80 percent $C_{12}$ to $C_{20}$. A more preferred distribution of alkyl chain lengths comprises from about 50 to about 70 percent $C_{12}$ to $C_{20}$.

The above method further employs, concurrently with or subsequent to the injection of the aqueous solution in step (a), injecting into the formation an amount of polymer effective for driving the aqueous solution of step (a) into the formation to displace the crude oil to thereby recover hydrocarbons from a production well.

In the above method, the polymer may be any suitable polymer, such as a polysaccharide, a polyacrylamide or a partially hydrolyzed polyacrylamide.

The above method further employs, concurrently with or subsequent to the injection of the aqueous solution in step (a), injecting into the formation an amount of water effective for driving the aqueous solution of step (a) into the formation to displace the crude oil to thereby recover hydrocarbons from a production well.

The above method further employs, concurrently with or subsequent to the injection of the polymer, injecting into the formation an amount of water effective for driving the aqueous solution of step (a) or the above polymer into the formation to displace the crude oil to thereby recover hydrocarbons from a production well.

In the above method, the hydrocarbon in the subterranean formation may include a waxy crude oil.

The aqueous solution in step (a) in the above method further employs a co-surfactant having a molecular weight in the range of about 60 to about 1,200.

The co-surfactant in the above method may be an alcohol (primary, secondary, tertiary or mixtures thereof), an alcohol ether, a polyalkylene glycol, a poly(oxyalkylene) glycol, a poly(oxyalkylene)glycol ether or mixtures thereof. The poly (oxyalkylene) gylcol ether may be any $C_1$-$C_8$ mono-alkyl ether, such as ethylene or propylene glycol mono-alkyl or mono-phenyl ether, a di-ethylene or di-propylene glycol mono-alkyl or mono-phenyl ether, a tri-ethylene or tri-propylene glycol mono-alkyl or mono-phenyl ether, poly-ethylene glycol mono-phenyl ether, polypropylene glycol mono-phenyl ether or mixtures thereof.

Examples of the poly(oxyalkylene) glycol are poly(oxyethylene) glycol and poly(oxypropylene) glycol or mixtures thereof.

In the above method in step (a) the co-surfactant is in the range of about 0.03 weight percent to about 2.0 weight percent of the total weight of the aqueous solution. Preferably, the co-surfactant is in the range of about 0.1 weight percent to about 1.5 weight percent of the total weight of the aqueous composition. More preferably, the co-surfactant is in the range of about 0.3 weight percent to about 1.0 weight percent of the total weight of the aqueous composition, and most preferably the co-surfactant is in the range of about 0.5 weight percent to about 0.8 weight percent of the total weight of the aqueous composition.

BRIEF DESRIPTION OF THE DRAWINGS

FIG. 3 is a plot of Equilibrated Interfacial Tensions, measured according to the method described below, versus sodium chloride concentration for samples of the alkylxylene sulfonate prepared using alkylxylene described in Examples 1A, 1B, 1C and 1D (using trifluoromethane sulfonic acid as the alkylation catalyst).

Figure 1:
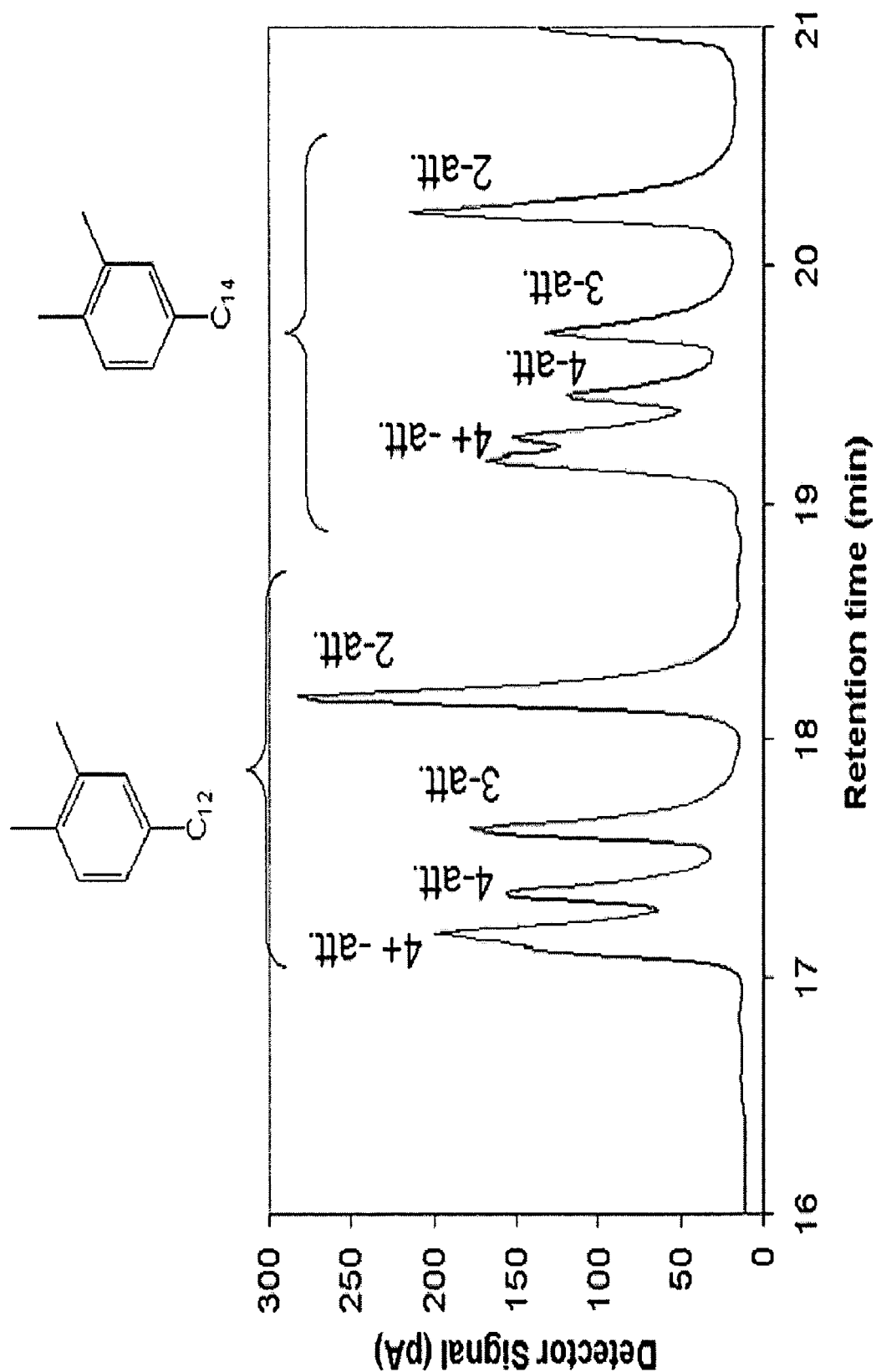
FIG. 1 is a chromatogram obtained by Gas Chromatography of a sample of the alkylxylene prepared using aluminum trichloride in Example 3A. The weight percent of the attachment at carbon positions 2, 3, 4 and 4+ for $C_{12}$ and $C_{14}$ carbon chains can be calculated from the area under the resolved peaks shown in the chromatogram.

FIG. 3 also shows IFT data for samples of the alkylxylene sulfonate prepared using alkylxylene described in Example 2 (using hydrogen fluoride as the alkylation catalyst), Example 3A (using aluminum trichloride as the alkylation catalyst) and Example 4 (using the ionic liquid alkylation catalyst).

DETAILED DESCRIPTION OF THE INVENTION

Definitions

As used herein, the following terms have the following meanings unless expressly stated to the contrary:

The terms "active" or "actives" as used herein refers to the concentration of sodium alkylxylene sulfonates in the Examples described in the present invention. The calculation of the actives content as sodium alkylxylene sulfonate is described in Example 6 and the data are summarized in Table II.

The term "alkylate" as used herein refers to the alkylxylene used to prepare the alkylxylene sulfonates of the present invention. The alkylxylene was prepared using xylene and linear alpha olefin or isomerized olefin containing from about 10 to about 58 carbon atoms. Preferably, the linear alpha olefin or isomerized olefin contains from about 10 to about 40 carbon atoms, and more preferably from about 12 to about 30 carbon atoms.

The term "alkali metal" as used herein refers to Group I A metals of the Periodic Table.

The term "alkoxide" means a compound which can be formed as the reaction product of an alcohol and a reactive metal.

The term "co-surfactant" herein refers to nonionic surfactants that are used in conjunction with anionic surfactants in enhanced oil recovery processes. Generally, nonionic surfactants have a somewhat higher tolerance to polyvalent ions, are water-soluble, and exhibit a wide range of low and stable interfacial tensions between alkaline brine and crude oil. They may also provide a reduction in viscosity of the surfactant.

The terms "enhanced oil recovery" or "EOR" as used herein refer to processes for enhancing the recovery of hydrocarbons from subterranean reservoirs. Techniques for improving displacement efficiency or sweep efficiency may be used for the exploitation of an oil field by introducing displacing fluids or gas into injection wells to drive oil through the reservoir to producing wells.

The terms "Gas Chromatography" or "GC" as used herein refer to Gas Liquid Phase Chromatography.

The terms "interfacial tension" or "IFT" as used herein refer to the surface tension between oil and water of different salinities. To achieve high enhanced oil recovery, it is necessary to reduce the interfacial tension between the oil and the water in the reservoir to about 0.01 dyne per centimeter. These ultra-low interfacial tensions are measured using a spinning drop tensiometer. Interfacial tension may be also measured by any known method for measuring interfacial tension.

The term "isomerized olefin" as used herein refers to an alpha olefin that has been subjected to isomerization conditions which results in an alternation of the distribution of the olefin species present and/or the introduction of branching along the alkyl chain.

The term "micro-emulsion" as used herein refers to a stable micellar solution of oil, water, a surfactant and optionally one or more electrolytes. Micro-emulsions are defined as those emulsions having an average particle size of about a few nanometers in diameter.

The term "neutralized" as used herein refers to alkylxylene sulfonic acid neutralized with an inorganic or an organic base, such as an alkali metal hydroxide, oxide and/or alkoxide, ammonia, an organic amine or an alkanol amine.

The terms "optimum salinity" or "midpoint salinity" as used herein refer to the amount of salt in the aqueous phase required to minimize the interfacial tension and maximize the recovery of oil.

The term "waxy crude oil" as used herein refers to crude oil usually consisting of a variety of light and intermediate hydrocarbons, such as paraffins and aromatic hydrocarbons, wax paraffins and a variety of other heavy organic compounds, such as resins and asphaltenes.

Unless otherwise specified, all percentages are in weight percent and the pressure is atmospheric pressure.

It has surprisingly been discovered that in the alkylxylene sulfonate of the present invention the attachment position of the alkyl group to the xylene moiety is important for obtaining low interfacial tension. The best results were obtained when the alkylxylene moiety in the alkylxylene sulfonate contains greater than 70 percent the 4-alkyl-1,2-dimethyl benzene based on the total alkylxylene sulfonate. Furthermore, the alkyl group attachment along the carbon chain of the alkyl group to the xylene moiety is also surprisingly important for obtaining low interfacial tension. Attachment of the alkyl group to the xylene moiety of the alkylxylene at positions higher than the 2-position along the alkyl carbon chain provides an EOR surfactant having low interfacial tension. It is preferred that at least 40 percent of the total alkylxylene sulfonate have the attachment at positions higher than the 2-position along the alkyl carbon chain. Gas Chromatography (GC) and $^{13}$C-Nuclear Magnetic Resonance spectroscopy ($^{13}$C-NMR) were used to determine the attachment position along the alkyl carbon chain.

Alkylxylene containing from about 10 to about 58 carbon atoms was prepared from ortho-xylene. Alkylation catalysts, hydrogen fluoride (HF), trifluoromethane sulfonic acid ($CF_3SO_3H$), aluminum trichloride ($AlCl_3$) and the ionic liquid catalyst, methyltributylammonium heptachloroaluminate, were used to alkylate ortho-xylene. The nature of the alkylation catalyst plays a key role in determining the alkylation position on the ortho-xylene ring. $^{13}$C-NMR analysis has shown that aluminum chloride and methyltributylammonium heptachloroaluminate typically give more than 90 percent yield of the 4-alkyl-1,2-dimethyl benzene (4-alkyl-ortho-xylene) based on the total amount of the alkylxylene produced. On the other hand, when hydrogen fluoride or trifluoromethane sulfonic acid is used as the alkylation catalyst, a mixture of 4-alkyl-1,2-dimethyl benzene (4-alkyl-ortho-xylene) and 3-alkyl-1,2-dimethyl benzene (3-alkyl-ortho-xylene) is obtained. Typically, the yield of the 4-alkyl-1,2-dimethyl benzene (4-alkyl-ortho-xylene) is about 70 percent based on the total amount of the alkylxylene produced.

It has also been observed that the attachment position along the carbon chain of the alkyl group to the xylene moiety is important for obtaining lower IFT data. Attachment of the alkyl group to the xylene moiety at positions higher than the 2-position along the alkyl carbon chain provides an EOR surfactant having lower IFT. It is preferred that at least 40 percent of the total alkylxylene sulfonate composition has attachment at positions higher than the 2-position along the alkyl carbon chain. GC and $^{13}$C-NMR were used to determine the attachment position along the alkyl carbon chain.

Alkylxylene sulfonate containing more than 40 percent attachment at positions higher than the 2-position along the alkyl carbon chain may be obtained by the use of pre-isomerized olefins containing internal double bonds.

It has been discovered that when the alkylxylene is prepared using the alkylation catalyst trifluoromethane sulfonic acid ($CF_3SO_3H$), the resultant alkylxylene sulfonate of the present invention has an optimum salinity at 0.5 percent sodium chloride. On the other hand, when aluminum trichloride ($AlCl_3$) is used for preparing the alkylxylene sulfonate of the present invention, the optimum salinity is 0.3 percent sodium chloride. The ionic liquid alkylation catalyst methyltributylammoniumchloride exhibits an optimum salinity at 0.4 percent sodium chloride. Thus, the alkylxylene sulfonate of the present invention may be effectively used for enhanced oil recovery in reservoirs with salinities varying between 0.2 to 0.5 percent.

The present invention is also directed to a method for enhancing the recovery of oil from a subterranean reservoir which method comprises injecting into the formation an aqueous solution containing an amount of the alkylxylene sulfonate or mixtures of alkylxylene sulfonates of the present invention effective for enhancing the recovery of crude oil.

In addition to the use of an aqueous solution containing the alkylxylene sulfonate of the present method for enhancing the recovery of crude oil, optionally, an amount of polymer may be injected, concurrently with or subsequent to the injection of the aqueous solution, effective for driving the aqueous solution of the alkylxylene sulfonate into the formation to displace the crude oil into the formation to recover hydrocarbons from a production well.

The injection of the polymer may be followed by an injection of an amount of water effective for driving the polymer into the formation to recover hydrocarbons from a production well. Alternately, the injection of an amount of water effective for driving the alkylxylene sulfonate of the present invention into the formation to recover hydrocarbons from a production well may be performed without the prior injection of the polymer. Another alternative involves the use of water along with the polymer for driving the alkylxylene sulfonate of the present invention into the formation to recover hydrocarbons from a production well.

In the above method, the hydrocarbon in the subterranean formation may be a waxy crude oil.

Any suitable co-surfactants may optionally be used with the alkylxylene sulfonate of the present invention. Examples of such suitable co-surfactants are alcohols, alcohol ethers, polyalkylene glycols, poly(oxyalkylene)glycols and poly(oxyalkylene)glycol ethers may optionally be used along with the alkylxylene sulfonate of this invention for surfactant flooding.

Preparation of Alkylxylenes

The alkylxylenes used for the preparation of the neutralized alkylxylene sulfonic acids of the present invention may be prepared with normal alpha olefins and isomerized olefins by any method known to a person skilled in the art.

Typically, alkylxylenes may be prepared using acid catalysts (Bronsted or Lewis acids), such as hydrogen fluoride, trifluoromethane sulfonic acid or aluminum trichloride. Trifluoromethane sulfonic acid can mimic hydrogen fluoride in alkylation reactions and its use is preferred in the laboratory to avoid the hazardous handling of hydrogen fluoride. Example 1 shows that the data obtained using trifluoromethane sulfonic acid as the alkylation catalyst correlates well with the data obtained in Example 2 using hydrogen fluoride as the alkylation catalyst.

The alkylation reaction is typically carried out with a xylene to olefin molar ratios from 1:15 to 25:1. Process temperatures can range from about 0° C. to about 200° C. As the olefins have a high boiling point, the process is preferably carried out in the liquid phase.

The alkylation process may be carried out in batch or continuous mode. In the batch mode, a typical method is to use a stirred autoclave or glass flask, which may be heated or cooled to the desired reaction temperature. At the end of the reaction, the catalyst is either recycled (when hydrogen fluoride is used) or hydrolyzed (when aluminum trichloride is used) or removed by washing (when trifluoromethane sulfonic acid is used).

Procedure for Isomerization of Normal Alpha Olefins

The isomerization of normal alpha olefins is achieved using at least two types of acidic catalysts, solid or liquid. A solid catalyst preferably has at least one metal oxide and an average pore size of less than 5.5 angstroms. More preferably, the solid catalyst is a molecular sieve with a one-dimensional pore system, such as SM-3, MAPO-11, SPO-11, SSZ-32, ZSM-23, MAPO-39, SAPO-39, ZSM-22 or SSZ-20. Other possible solid acidic catalysts useful for isomerization include ZSM-35, SUZ4, NU-23, NU-87 and natural or synthetic ferrierites. These molecular sieves are well known in the art and are discussed in Rosemarie Szostak's Handbook of molecular Sieves (New York, Van Nostrand Reinhold, 1992 and U.S. Pat. No. 5,282,858, which are hereby incorporated by reference for all purposes. A liquid type of isomerization catalyst that can be used is iron pentacarbonyl ($Fe(CO)_5$).

The process for the isomerization of normal alpha olefins may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (alpha olefin, beta olefin; internal olefin, tri-substituted olefin, and vinylidene olefin) and branching content than the unisomerized olefin and conditions are selected in order to obtain the desired olefin distribution and the degree of branching.

Procedure for Sulfonation of Alkylxylene

Sulfonation of alkylxylene may be carried out by any method known to a person skilled in the art.

The sulfonation reaction is typically carried out in a falling film tubular reactor maintained at about 55° C. The alkylxylene is placed in the reactor tube along with sulfur trioxide diluted with air. The molar ratio of alkylxylene to sulfur trioxide is maintained at about 1.05:1.

Procedure for Neutralization of Alkylxylene Sulfonic acids

Neutralization of alkylxylene sulfonic acids may be carried out in a continuous or batch process by any method known to a person skilled in the art to produce alkylxylene sulfonates.

Generally, the neutralization reaction is carried out in an in-line mixing reactor in which the alkylxylene sulfonic acid and an organic or inorganic base are mixed and the temperature is maintained between about 20° C. and 80° C. The amount of alkali metal used is based on the acid number determined for each alkylxylene sulfonic acid.

EXAMPLES

Example 1

Preparation of Alkylxylene using Trifluoromethane Sulfonic Acid Alkylation Catalyst Example 1A Alkylation of Ortho-xylene with $C_{10}$-$C_{58}$ Normal Alpha Olefins Alkylxylene was prepared using trifluoromethane sulfonic acid alkylation catalyst. To a 3 liter glass reactor were charged, under nitrogen, 904.09 grams of ortho-xylene and 595.91 grams of $C_{10}$-$C_{58}$ normal alpha olefin and allowed to mix. The mixture was heated to 60° C. Next, 41.71 grams of trifluoromethane sulfonic acid was added to the reaction mixture while stirring. A strong exotherm was observed with a temperature increase to 122° C. The reaction mixture was allowed to cool to room temperature for 4 hours and 30 minutes. After this cooling period, the reaction was quenched with cold distilled water followed by three consecutive water washes to remove the acid catalyst from the organic phase. The organic phase containing the alkylxylene product was dried over magnesium sulfate and the excess ortho-xylene was distilled under reduced pressure using a Rotovap evaporator to recover the alkylxylene product.

Example 1B

Alkylation of Ortho-xylene with $C_{10}$-$C_{58}$ Isomerized Olefin

Alkylxylene was prepared using trifluoromethane sulfonic acid alkylation catalyst. To a 3 liter glass reactor were charged, under nitrogen, 852 grams of ortho-xylene and 600 grams of $C_{10}$-$C_{58}$ isomerized olefin (normal alpha olefin content about 75 percent of the total olefin) and allowed to mix. The reaction mixture was heated to 40° C. Next, 42 grams of trifluoromethane sulfonic acid was added to the reaction mixture while stirring. A strong exotherm was observed with a temperature increase to 90° C. The reaction mixture was allowed to cool 60° C. and held at this temperature for 2 hours. After this cooling period, the reaction was quenched and the alkylxylene was recovered as described above in Example 1A.

Example 1C

Alkylation of Ortho-xylene with $C_{10}$-$C_{58}$ Isomerized Olefin

Alkylxylene was prepared using trifluoromethane sulfonic acid alkylation catalyst. To a 3 liter glass reactor were charged, under nitrogen, 852 grams of ortho-xylene and 600 grams of $C_{10}$-$C_{58}$ isomerized olefin (normal alpha olefin content about 40 percent of the total olefin) and allowed to mix. The reaction mixture was heated to 40° C. Next, 42 grams of trifluoromethane sulfonic acid was added to the reaction mixture while stirring. A strong exotherm was observed with a temperature increase to 90° C. The reaction mixture was allowed to cool 60° C. and held at this temperature for 2 hours. After this cooling period, the reaction was quenched and the alkylxylene was recovered as described above in Example 1A.

Example 1D

Alkylation of Ortho-xylene with $C_{10}$-$C_{58}$ Isomerized Olefin

Alkylxylene was prepared using trifluoromethane sulfonic acid alkylation catalyst. To a 3 liter glass reactor were charged, under nitrogen, 852 grams of ortho-xylene and 600 grams of $C_{10}$-$C_{58}$ isomerized olefin (normal alpha olefin content about 5 percent of the total olefin) and allowed to mix. The reaction mixture was heated to 40° C. Next, 42 grams of trifluoromethane sulfonic acid was added to the reaction mixture while stirring. A strong exotherm was observed with a temperature increase to 90° C. The reaction mixture was allowed to cool 60° C. and held at this temperature for 2 hours. After this cooling period, the reaction was quenched and the alkylxylene was recovered as described above in Example 1A.

Example 2

Preparation of Alkylxylene using Hydrogen Fluoride Alkylation Catalyst

Example 2

Alkylation of Ortho-xylene with $C_{10}$-$C_{58}$ Normal Alpha Olefin

Alkylxylene was prepared using hydrogen fluoride as alkylation catalyst. Ortho-xylene was alkylated with of $C_{10}$-$C_{58}$ normal alpha olefin in a continuous process alkylation pilot plant. The pilot plant consisted of a stirred, heat-jacketed reactor (1.15 liters) in series with a settler (25 liters). The settler is for separating the organic phase from the phase containing the hydrofluoric acid and is maintained under nitrogen pressure of approximately $5 \times 10^5$ pascal (72.52 psi). $C_{10}$-$C_{58}$ normal alpha olefins heated to approximately 50° C. was pumped into the reactor heated to approximately 64° C. at a rate of approximately 16.3 grams per minute. Simultaneously with the addition of the normal alpha olefins, hydrofluoric acid was charged to the reactor at a rate of approximately 1.7 grams per minutes along with ortho-xylene at a rate of approximately 58 grams per minute. The charge mole ratio of the ortho-xylene to the normal alpha olefins was 10 and the charge mole ratio of the hydrofluoric acid to the normal alpha olefins was 1.5. The residence time in the reactor was approximately 15 minutes. The resulting product mixture was passed into the unheated settler and depressurized to atmospheric pressure. The organic layer was recovered from the settler and the excess ortho-xylene removed by distillation to obtain the alkylated ortho-xylene.

Example 3

Preparation of Alkylxylene using Aluminum Trichloride Alkylation Catalyst

Example 3A

Alkylation of Ortho-xylene with $C_{10}$-$C_{58}$ Normal Alpha Olefins

Alkylxylene was prepared using aluminum trichloride alkylation catalyst by a contract manufacturer in a continuous process using ortho-xylene and $C_{10}$-$C_{58}$ normal alpha olefins.

Example 3B

Alkylation of Ortho-xylene with $C_{10}$-$C_{58}$ Normal Alpha Olefins

Into a 3 liter glass reactor were charged, under nitrogen, 711.3 grams of ortho-xylene and while stirring 35.7 grams of aluminum trichloride was added to the reaction mixture. Next, 357.7 grams of $C_{10}$-$C_{58}$ normal alpha olefin was added to the reactor over 3 hours in order to control the temperature increase due to the exothermic reaction. The temperature of the reaction mixture never exceeded 21° C. At the end of the olefin addition, the reaction mixture was maintained at about 20° C. with continued stirring for one hour. After this period, the reaction was quenched and the alkylxylene was recovered as described above in Example 1A except that a 3.0 weight percent ammonium hydroxide aqueous solution was used for the first two washes of the organic phase to remove the aluminum from the organic phase by solubilizing it in the aqueous phase.

Example 3C

Alkylation of Ortho-xylene with $C_{10}$-$C_{58}$ Normal Alpha Olefins

To a 3 liter glass reactor were charged, under nitrogen, 682.8 grams of ortho-xylene and while stirring 28.6 grams of aluminum trichloride was added to the reaction mixture. The temperature of the reaction mixture at this time was about 20° C. Next, 572.4 grams of $C_{10}$-$C_{58}$ normal alpha olefin was added to the reactor over about 15 minutes. The temperature of the reaction mixture spiked to 76° C. The reaction mixture was cooled to about 60° C. and the alkylation reaction was allowed to proceed at this temperature for two hours. After this period, the reaction was quenched and the alkylxylene was recovered as described above in Example 3B.

Example 4

Preparation of Alkylxylene using an Ionic Liquid Alkylation Catalyst Alkylation of Ortho-xylene with $C_{10}$-$C_{58}$ Normal Alpha Olefins An ionic liquid alkylation catalyst was prepared by mixing 1 mole of methyltributylammoniumchloride with 2 moles of aluminum chloride under nitrogen. From the reaction was obtained 36.6 milliliters of the ionic liquid alkylation catalyst as a brown ionic liquid. The ionic liquid alkylation catalyst was charged to a glass reactor under nitrogen. To 183.2 grams of $C_{10}$-$C_{58}$ normal alpha olefin was mixed 166.8 grams of ortho-xylene. The mixture was added slowly to the ionic liquid alkylation catalyst while stirring at room temperature over about 15 minutes. The temperature of the reaction mixture spiked to 80° C. because of the exothermic reaction. The reaction mixture was allowed to slowly cool down to room temperature while being stirred for an additional 2 hours. Next, the reaction mixture was washed 3 times with water and the alkylxylene was recovered as described above in Example 3B.

Example 5

Preparation of Alkylxylene Sulfonic Acids

Alkylxylene sulfonic acids were prepared using the alkylxylenes prepared in Examples 1-4 above.

Sulfonation of the alkylxylene was performed in a continuous falling film flow reactor by contacting the alkylxylene with a stream of air and sulfur trioxide. The molar ratio of the alkylxylene to sulfur trioxide was about 1:0.94. The reactor jacket temperature was maintained around 55° C. The sulfonic acid product was titrated potentiometrically with a standardized cyclohexylamine solution to determine the weight percent of the sulfonic acid and the sulfuric acid in the samples. The total acid number was also determined using the ASTM Test No. D-664. The results are summarized below in Table I. Two samples of the alkylxylene prepared in Examples 1A, 1B, 1C, 1D and 2 were sulfonated as described above. The duplicate samples of these alkylxylene sulfonates are shown as 1A', 1B', 1C', 1D' and 2' in Tables I and II below.

TABLE I

| Example | Catalyst | $RSO_3H$* (weight %) | $H_2SO_4$ (weight %) | Acid Number (mg KOH/g) |
|---|---|---|---|---|
| Example 1A | $CF_3SO_3H$ | 86.8 | 0.77 | 128 |
| Example 1A' | $CF_3SO_3H$ | 88.9 | 0.82 | 128 |
| Example 1B | $CF_3SO_3H$ | 83.9 | 0.92 | 124 |
| Example 1B' | $CF_3SO_3H$ | 84.4 | 0.91 | 124 |
| Example 1C | $CF_3SO_3H$ | 83.7 | 0.96 | 124 |
| Example 1C' | $CF_3SO_3H$ | 83.9 | 0.93 | 120 |
| Example 1D | $CF_3SO_3H$ | 82.3 | 1.07 | 122 |
| Example 1D' | $CF_3SO_3H$ | 82.5 | 1.10 | 125 |
| Example 2 | HF | 90.5 | 0.62 | 126 |
| Example 2' | HF | 86.8 | 0.71 | 124 |
| Example 3A | $AlCl_3$ | 86.4 | 0.93 | 118 |
| Example 3B | $AlCl_3$ | 75.5 | 0.91 | 109 |
| Example 3C | $AlCl_3$ | 78.7 | 1.04 | 113 |
| Example 4 | Ionic Liquid | 89.3 | 0.82 | 129 |

*An average molecular weight of 453 grams per mole is assumed for all the sulfonic acids.

Example 6

Preparation of Alkylxylene Sulfonates

The alkylxylene sulfonates were prepared using the alkylxylene sulfonic acids prepared in Example 5 above.

Neutralization of the sulfonic acid was performed in a beaker with magnetic stirring. The sulfonic acid was heated to about 40° C. to lower the viscosity of the sulfonic acid. Next, a 50 weight percent solution of sodium hydroxide was slowly added to the reaction mixture. The temperature of the reaction mixture was maintained below 80° C. to control the evaporation of water. The sodium hydroxide added was calculated based on the acid number obtained for each sulfonic acid. To prepare the alkylxylene sulfonates, the exact amount of sodium hydroxide necessary for the neutralization of all the acid species in the sulfonic acid samples, sulfonic acid and $H_2SO_4$ was added to the reaction mixture based on the Total Acid Number analysis results obtained for the sulfonic acids reported in Table II below. An exact quantity of sodium hydroxide was employed to obtain exactly a 100 percent neutralization of the alkylxylene sulfonic acids.

The active content of the sodium alkylxylene sulfonate was calculated using the formula given below:

$$\% \text{ active as sodium sulfonate} = \frac{W_{SA} * W \%_{RSO_3H} * \frac{Mw_{RSO_3Na}}{Mw_{RSO_3H}}}{W_{SA} + W_{NaOH\,sol} * \left(1 + \frac{0.5 * 18}{40}\right)}$$

$W_{SA}$: Weight of sulfonic acid sample (grams)

$W \%_{RSO_3H}$: Weight percent of alkylxylene sulfonic acid determined by the cyclohexylamine titration $Mw_{RSO_3Na}$: Molecular weight of the alkylxylene sodium sulfonate (grams per mole)

$Mw_{RSO_3H}$: Molecular weight of the alkylxylene sulfonic acid (grams per mole)

$W_{NaOH\,sol}$: Weight of the NaOH solution (50 weight %) used for the neutralization surfactant having low IFT.

The average molecular weight of 475 g/mol was used for the alkylxylene sodium sulfonate.

The neutralization and actives content data collected for the neutralized alkylxylene sulfonates prepared in Example 6 are summarized below in Table II.

TABLE II

| Example | Alkylation catalyst | Weight of Sulfonic Acid (g) | Total Acid Number-TAN (mg KOH/g) | NaOH (50% weight in H$_2$O) | Active Content (weight %) |
|---|---|---|---|---|---|
| Example 1A | CF$_3$SO$_3$H | 241 | 128 | 44.0 | 74.4 |
| Example 1A' | CF$_3$SO$_3$H | 241 | 128 | 44.0 | 76.2 |
| Example 1B | CF$_3$SO$_3$H | 240 | 124 | 42.4 | 72.3 |
| Example 1B' | CF$_3$SO$_3$H | 240 | 124 | 42.4 | 72.7 |
| Example 1C | CF$_3$SO$_3$H | 240 | 124 | 41.1 | 72.7 |
| Example 1C' | CF$_3$SO$_3$H | 240 | 120 | 42.44 | 72.1 |
| Example 1D | CF$_3$SO$_3$H | 240 | 122 | 41.8 | 71.1 |
| Example 1D' | CF$_3$SO$_3$H | 240 | 125 | 42.8 | 71.0 |
| Example 2 | HF | 240 | 126 | 43.1 | 77.7 |
| Example 2' | HF | 246 | 124 | 41.8 | 74.8 |
| Example 3A | AlCl$_3$ | 240 | 118 | 40.4 | 75.1 |
| Example 3B | AlCl$_3$ | 50 | 109 | 7.76 | 66.5 |
| Example 3C | AlCl$_3$ | 50 | 113 | 8.09 | 68.9 |
| Example 4 | Ionic Liquid | 241 | 129 | 44.3 | 76.4 |

Example 7

Determination of the Attachment Position on the Alkyl Carbon Chain to the Xylene Moiety The attachment position on the alkyl carbon chain to the xylene moiety was determined by Gas Chromatography (GC) and quantitative $^{13}$C-Nuclear Magnetic Resonance spectroscopy ($^{13}$C-NMR).

Since the resolution of the peaks obtained in GC decreases with the retention time, it is possible to accurately quantify the attachment position of alkyl group on the xylene ring only for C$_{12}$ and C$_{14}$ carbon alkyl chains. Quantitative $^{13}$C-NMR on the other hand provides an average value for all carbon atoms on the alkyl chain lengths.

Figure 2:
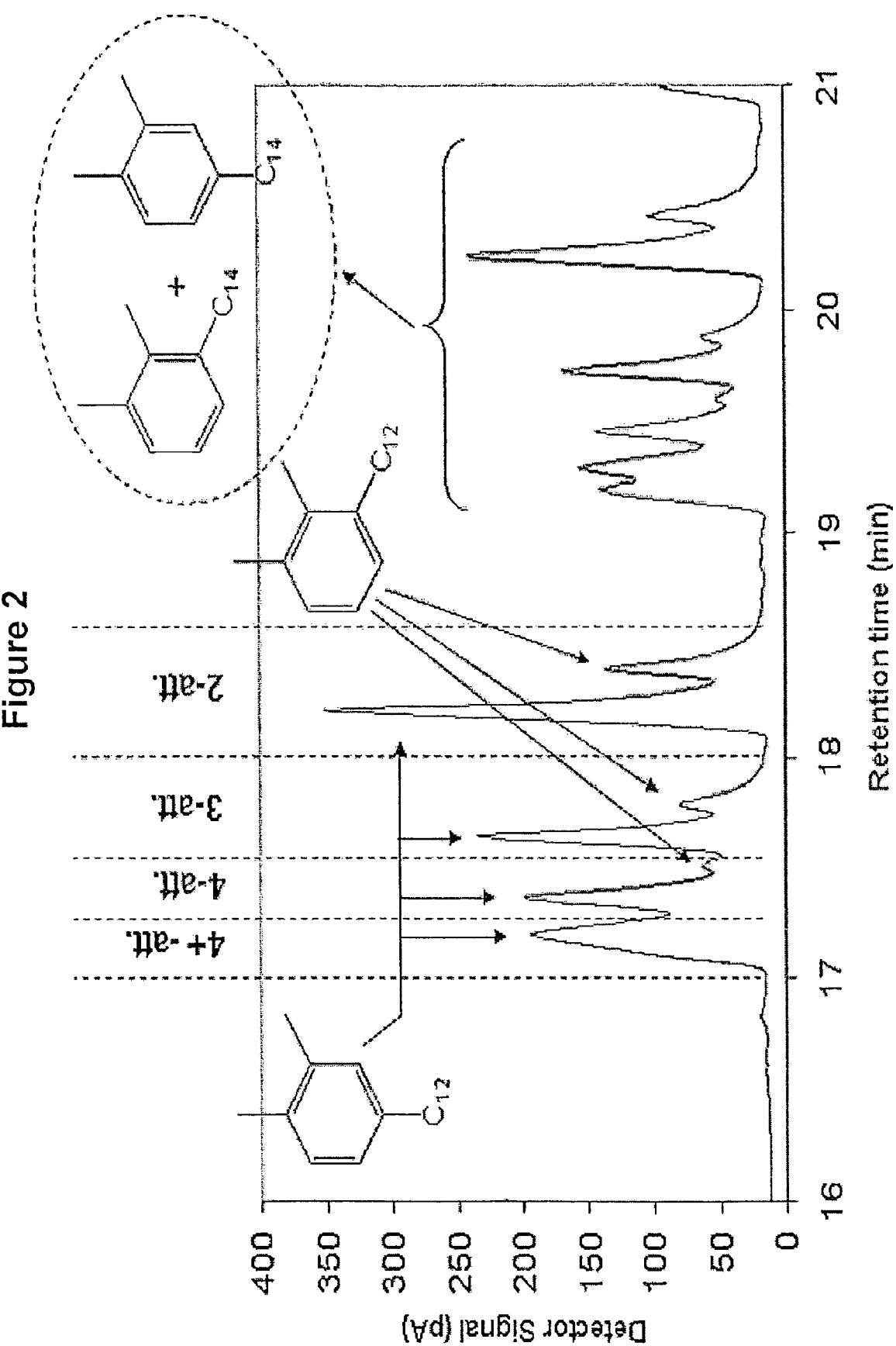
FIG. 2 is similar to FIG. 1 and was obtained on a sample of the alkylxylene prepared using trifluoromethane sulfonic acid in Example 1A.

$^{13}$C-NMR and GC also give the attachment position of the alkyl chain on the ortho-xylene ring. It appears that when aluminum trichloride is used to catalyze the alkylation of ortho-xylene, the isomer formed primarily is 4-alkyl-1,2-dimethyl benzene, whereas when trifluoromethane sulfonic acid or hydrogen fluoride are use as alkylation catalysts a mixture of 3-alkyl-1,2-dimethyl benzene and 4-alkyl-1,2-dimethyl benzene is obtained. FIGS. 1 and 2 show the C$_{12}$ and C$_{14}$ portion of the gas chromatograms obtained for the alkylate prepared in Examples 1A and 3A, respectively. The percent of the 4-alkyl-1,2-dimethyl benzene was calculated based by averaging the area of the GC peaks for the 2-position attachment on the alkyl chain for C$_{12}$ and C$_{14}$. The attachment position of the xylene ring on the alkyl carbon chain of the alkyl group was also calculated. The GC results obtained for Examples 1-4 are given below in Table II. The data show that percent of the 4-alkyl-1,2-dimethyl benzene is much lower in Examples 1 and 2 when the alkylation catalyst is trifluoromethane sulfonic acid or hydrogen fluoride than in Examples 3 and 4 when aluminum trichloride or ionic liquid catalyst is used as the alkylation catalyst.

The GC data obtained for Examples 3B and 3C in Table III also show that the alkylation reaction is temperature dependent. The samples prepared in Examples 3B and 3C were treated similarly except that the temperature of the alkylation reaction in 3B was controlled at about 20° C. by addition of the normal alpha olefin over a 3 hour period to prevent the temperature from increasing due to the exotherm of the alkylation reaction. In contrast, in Example 3C, the normal alpha olefin was added over about 15 minutes and the temperature spiked to 76° C. with the result that the sample in Example 3C contains nearly twice as much of the 3-4+alkyl chain attachment compared to the sample prepared in Example 3B. The 3-4+alkyl chain attachment in Examples 3B and 3C is 36.7 and 68.1 percent of the total attachment, respectively. It is believed that the alkylation catalysts, such as aluminum trichloride, also catalyze isomerization of the olefin to produce olefins containing a higher percentage of internal double bonds and at high temperatures the isomerization reaction proceeds at a faster rate than at low temperatures.

TABLE III

| Example | Alkylation Catalyst | 4-alkyl-1,2-dimethyl-benzene (% of total alkyl-ortho-xylene) | Alkyl Chain Attachment position | | | |
|---|---|---|---|---|---|---|
| | | | 2 | 3 | 4 | 4+ | 3-4+ |
| Example 1A | CF$_3$SO$_3$H | 73 | 35.8 | 21.1 | 17.9 | 25.2 | 64.2 |
| Example 1B | CF$_3$SO$_3$H | 71 | 33.9 | 22.2 | 18.7 | 25.2 | 66.1 |
| Example 1C | CF$_3$SO$_3$H | 65 | 27.9 | 21.2 | 20.3 | 30.6 | 72.1 |
| Example 1D | CF$_3$SO$_3$H | 71 | 16.1 | 11.9 | 21.9 | 50.1 | 83.9 |
| Example 2 | HF | 64 | 25.9 | 20.1 | 20 | 34 | 74.1 |
| Example 3A | AlCl$_3$ | >95 | 50.1 | 21.9 | 11.9 | 16.1 | 49.9 |
| Example 3A* | AlCl$_3$ | >95 | 46.5 | 18.8 | 14.9 | 19.8 | 53.5 |
| Example 3B | AlCl$_3$ | >95 | 63.4 | 21.9 | 7.8 | 7.0 | 36.7 |
| Example 3C | AlCl$_3$ | >95 | 32.0 | 19.4 | 16.8 | 31.9 | 68.1 |
| Example 4 | Ionic Liquid | >95 | 30.3 | 16.3 | 19.3 | 34.2 | 69.7 |

*The alkyl chain attachment position to the xylene moiety was also determined by $^{13}$C-NMR for the alkylxylene prepared in Example 3A.

Example 8

Determination of Interfacial Tension

The performance of the alkylxylene sulfonates prepared above in Example 6 was determined by measuring the interfacial tension. The alkylxylene sulfonates in Example 6 were prepared using the alkylxylene sulfonic acids prepared in Example 5, which in turn were prepared using the alkylxylenes prepared in Examples 1-4.

Alkylxylene sulfonates prepared from alkylxylenes prepared in Example 1C, Example 2 and Example 3B were used for comparison since they are outside the scope of the alkylxylene sulfonates of the present invention.

The interfacial tension was determined using Minas crude oil (a waxy crude oil) having a pour point around 35° C. and aqueous solutions of the alkylxylene sulfonates. A spinning drop tensiometer was used to measure the interfacial tension at 93° C. Two methods described below were used to measure the interfacial tension:

Equilibrated Interfacial Tension Method

A 5 milliliter sample of a solution of alkylxylene sulfonate, water, a co-surfactant and sodium chloride was added to an equal volume of crude oil in a glass tube. The test tube was tightly sealed and shaken. The test tube was allowed to equilibrate for one month at 93° C. At the end of the equilibration period, an aliquot of aqueous phase was loaded into the glass tube of the spinning tensiometer. Next, a small drop of the upper oil phase is injected into the glass tube. The tube is spun and the interfacial tension between the aqueous solution and the oil is determined using the B. Vonnegut equation for elongated droplets given in B. Vonnegut in *Review Scientific Instruments,* 13 (1942) 6:

$$IFT = \frac{w^2 R^3 \Delta\rho}{4}$$

ω being the rotational speed, R the radius of the droplet, and Δρ the density difference between the oil and the aqueous solution. It takes typically 1 to 3 hours for the system to reach equilibrium.

Fresh Interfacial Tension Method

Interfacial tension is measured as described above except without the equilibrium period of one month at 93° C. The glass tube of the spinning tensiometer is filled as described above with a solution of alkylxylene sulfonate, water, a co-surfactant and sodium chloride and sealed. A drop of oil is injected into the sealed glass tube. The tube is spun and the interfacial tension is recorded until a stable value is obtained, which takes generally 1 to 3 hours. Although this method can be used to obtain interfacial tension data in only a few hours, the data obtained by this method tend to be higher than those obtained using the Equilibrated Interfacial Tension Method described above.

Interfacial tension data for the alkylxylene sulfonates prepared above in Example 6 were determined using the Equilibrated Interfacial Tension Method described above. Samples were prepared with 0.24 weight percent (on active basis) of the alkylxylene sulfonate and 0.067 weight percent sec-butyl alcohol as co-surfactant. The interfacial tension data were collected in the presence of sodium chloride solutions between 0.1 percent to 0.5 percent.

The results of the interfacial tension determination are given below in Tables IV and V.

TABLE IV

| Example | 4-alkyl-1,2-dimethyl-benzene (% of total alkyl-ortho-xylene) | 3,4 & 4+ Position on Carbon Chain* (% of total attachment) | Salinity (weight % NaCl) IFT (dynes/cm) | | | | |
|---|---|---|---|---|---|---|---|
| | | | 0.1 | 0.2 | 0.3 | 0.4 | 0.5 |
| Example 1A | 73 | 64.2 | 2.75 | 0.81 | 0.28 | 0.051 | 0.006 |
| Example 1B | 71 | 66.1 | 5.61 | 0.97 | 0.67 | 0.154 | 0.00075 |
| Example 1D | 71 | 83.9 | 1.88 | 0.49 | 0.047 | 0.00035 | 0.00022 |
| Example 1C (comparative) | 65 | 72.1 | 3.34 | 1.21 | 1.05 | 0.118 | 0.018 |
| Example 2 (comparative) | 64 | 74.1 | 5.67 | 0.91 | 0.48 | 0.034 | 0.0275 |
| Example 3A | >95 | 49.9 | 1.71 | 0.009 | 0.002 | 0.09 | 0.089 |
| Example 4 | >95 | 69.7 | 0.49 | 0.03 | 0.009 | 0.00078 | 0.00083 |

*The percent attachment in the 3,4 and 4+ positions plus the percent attachment in the 2-position is a 100 percent.

Fresh interfacial tension data were used to compare the alkylxylene sulfonates prepared from the alkylxylene prepared in Examples 3B and 3C. Samples were prepared with 0.60 weight percent (on active basis) of the alkylxylene sulfonate and 0.17 weight percent sec-butyl alcohol as co-surfactant.

The fresh interfacial tension data were collected using a synthetic Minas oil field brine instead of the sodium chloride solution used in the equilibrated interfacial tension experiments described above. The composition of the synthetic Minas brine is given below:

| Component | Milligrams per liter | Milliequivalents per liter |
|---|---|---|
| Sodium (Na$^+$) | 900 | 39.13 |
| Calcium (Ca$^{+2}$) | 20 | 1.0 |
| Magnesium (Mg$^{+2}$) | 5 | 0.42 |
| Total Cation | | 40.55 |
| Chloride (Cl$^-$) | 800 | 22.57 |
| Bicarbonate (HCO$_3^-$) | 1100 | 18.03 |
| Sulfate (SO$_4^{-2}$) | 18 | 0.38 |
| Total Anion | | 40.98 |

Results of the fresh interfacial tension measurement summarized in Table V below show that the alkylxylene sulfonate prepared from the alkylxylene prepared in Example 3C is four times better than the alkylxylene prepared from the alkylxylene prepared in Example 3B. The data show that even when the 4-alkyl-1,2-dimethyl benzene isomer is very high in the alkylxylene sulfonates, greater than 95 percent of the total attachment, the interfacial tension is high if the amount of the 3, 4 and 4+ attachment on the alkyl carbon chain is low.

TABLE V

| Example | 4-alkyl-1,2-dimethyl benzene (% of total alkyl-ortho-xylene) | 3,4 & 4+ Position on Alkyl Carbon Chain (% of total attachment) | Fresh IFT in synthetic Minas brine (dynes/cm) |
|---|---|---|---|
| Example 3B (comparative) | >95 | 36.7 | 0.45 |
| Example 3C | >95 | 68.1 | 0.11 |

What is claimed is:

1. An alkylxylene sulfonate for enhanced oil recovery processes, having the general formula:

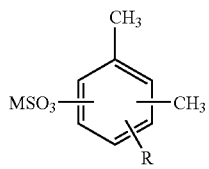

wherein R is an alkyl group containing from about 10 to about 58 carbon atoms, M is a mono-valent cation, and the alkylxylene moiety is alkyl-ortho-xylene in at least 85 percent of the total alkylxylene sulfonate and wherein the alkylxylene moiety in the alkylxylene sulfonate contains greater than about 70 percent of the 4-alkyl-1,2-dimethyl benzene isomer and the attachment of the alkyl group to the xylene moiety in the alkylxylene sulfonate is at positions higher than the 2-position along the alkyl chain in at least 40 percent of the total alkylxylene sulfonate, and wherein the alkyl group contains a distribution of alkyl chain lengths wherein the alkyl chain lengths comprise from about 40 to about 80 percent $C_{12}$ to $C_{20}$ and about 5 percent to about 15 percent of $C_{32}$ to $C_{58}$, and further wherein the optimum salinity of the alkylxylene sulfonate is in the range of 0.1 to 0.5 weight percent sodium chloride.

2. The alkylxylene sulfonate of claim 1, wherein the optimum salinity of the alkylxylene sulfonate is in the range of 0.2 to 0.5 weight percent sodium chloride.

3. The alkylxylene sulfonate of claim 2, wherein the optimum salinity of the alkylxylene sulfonate is in the range of 0.3 to 0.4 weight percent sodium chloride.

4. The alkylxylene sulfonate of claim 3, wherein the optimum salinity of the alkylxylene sulfonate is about 0.3 weight percent sodium chloride.

5. The alkylxylene sulfonate of claim 1, wherein the alkylxylene moiety in the alkylxylene sulfonate contains greater than about 80 percent of the 4-alkyl-1,2-dimethyl benzene isomer.

6. The alkylxylene sulfonate of claim 5, wherein the alkylxylene moiety in the alkylxylene sulfonate contains at least 90 percent of the 4-alkyl-1,2-dimethyl benzene isomer.

7. The alkylxylene sulfonate of claim 1, wherein the alkyl group on the xylene moiety is attached at positions higher than the 2-position along the alkyl chain in at least 45 percent of the total alkylxylene sulfonate.

8. The alkylxylene sulfonate of claim 7, wherein the alkyl group on the xylene moiety is attached at positions higher than the 2-position along the alkyl chain in at least 60 percent of the total alkylxylene sulfonate.

9. The alkylxylene sulfonate of claim 1, wherein the mono-valent cation is an alkali metal.

10. The alkylxylene sulfonate of claim 9, wherein the alkali metal is sodium.

11. The alkylxylene sulfonate of claim 1, wherein the alkyl group is derived from a linear alpha olefin or an isomerized olefin containing from about 10 to about 58 carbon atoms.

12. The alkylxylene sulfonate of claim 11, wherein the alkyl group is derived from a linear alpha olefin or an isomerized olefin containing from about 10 to about 40 carbon atoms.

13. The alkylxylene sulfonate of claim 1, wherein the alkyl chain lengths comprise from about 50 to about 70 percent $C_{12}$ to $C_{20}$ and about 5 percent to about 15 percent of $C_{32}$ to $C_{58}$.

14. The alkylxylene sulfonate of claim 13, wherein the alkyl chain lengths comprise about 8 percent to about 12 percent of $C_{32}$ to $C_{58}$.

15. The alkylxylene sulfonate of claim 1, wherein the alkylxylene moiety is alkyl-ortho-xylene in at least 95 percent of the total alkylxylene sulfonate.

16. The alkylxylene sulfonate of claim 1, wherein the mono-valent cation is an ammonium ion or an organic ammonium ion.

* * * * *